United States Patent [19]

Meilland

[11] Patent Number: Plant 7,384

[45] Date of Patent: Nov. 27, 1990

[54] ROSE PLANT — MEINOFRAI VARIETY

[75] Inventor: Alain A. Meilland, Antibes, France

[73] Assignee: The Conard-Pyle Company, West Grove, Pa.

[21] Appl. No.: 406,916

[22] Filed: Sep. 13, 1989

[51] Int. Cl.[5] ..... A01H 5/00
[52] U.S. Cl. ..... Plt./010
[58] Field of Search ..... Plt. 10

*Primary Examiner*—James R. Feyrer
*Attorney, Agent, or Firm*—Burns, Doane, Swecker & Mathis

[57] ABSTRACT

A new and distinct variety of rose plant of the Miniature Class is provided which forms abundantly and continuously attractive long lasting double blossoms. The blossoms are current red on the upper surface and cardinal red on the lower surface. The plant is bushy, exhibits a compact and regular growth habit, and forms very vigorous vegetation. The plant is well adapted to greenhouse forcing while grown in small containers, and to the low light and low humidity growing conditions commonly encountered in a home. Additionally, the plant is not particularly affected by crytogamic diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the Anytime variety (non-patented in the Untied States) by the Meichanso variety (nonpatented in the United States). The Meichanso variety is sometimes known as the Parador variety. The male parent (i.e., the pollan parent) of the new variety was the Mogral variety (non-patented in the United States). The parentage of the new variety can be summarized as follows:

[Anytime × Meichanso] × Mogral.

The seeds resulting from the above pollination were sown and 47 plantlets were obtained which were physically and biologicaly different from each other. Selective study resulted in the identification of a single plant of the new variety.

It was found that the new variety of Miniature rose plant of the present invention possesses the following combination of characteristics:

(a) forms in abundance on a continuous basis attractive double long lasting blossoms which are currant red on the upper surface and cardinal red on the lower surface,
(b) forms very vigorous vegetation,
(c) exhibits a compact, regular, and bushy growth habit,
(d) is well adapted to greenhouse forcing while growing in small containers and to the low light and low humidity growing conditions commonly encountered in the home, and
(e) is not particularly affected by crytogamic diseases.

The new variety well meets the needs of the horticultural industry for all usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Memofrai variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during February while growing on their own roots in greenhouse at Le Cannet des Maures, Var, France.

DETAILED DESCRIPTION

Figures 1, 2, 3, 4, 5, 6, 7, 8, 9, 10, 11, 12, 13, 14, 15, 16:
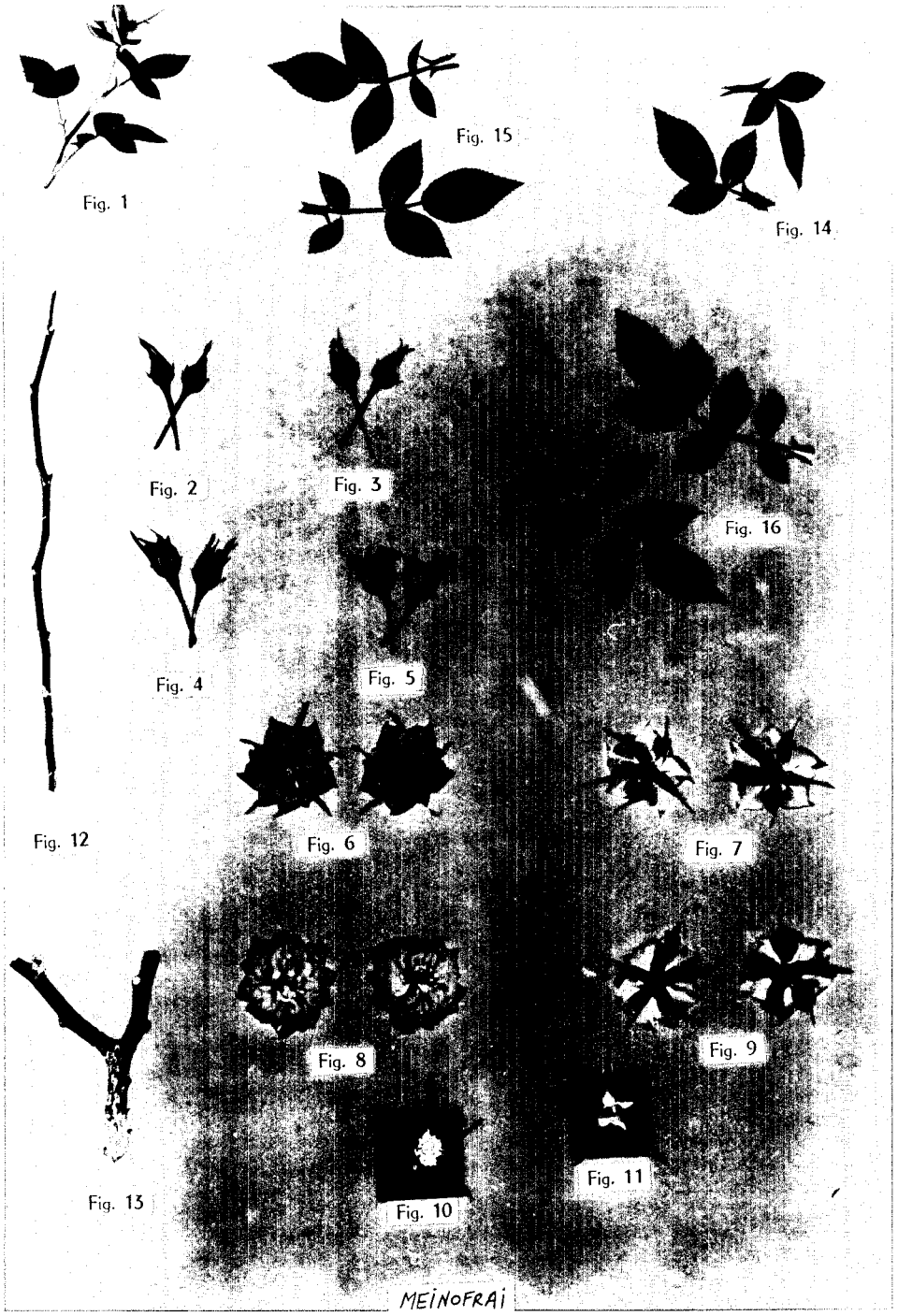
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates a specimen of two flowers in the course of opening.
FIG. 6 illustrates specimens of two flowers in the course of opening — plan view — obverse.
FIG. 7 illustrates specimens of two flowers in the course of opening — plan view — reverse.
FIG. 8 illustrates speciemsn of two fully open flowers — plan view — obverse.
FIG. 9 illustrates specimens of two fully open flowers — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown on the top right and the under surface being shown on the lower left.
FIG. 15 illustrates specimens of leaves with five leaflets with the upper surface being shown on the top and the under surface being shown on the bottom.
FIG. 16 illustrates specimens of leaves with seven leaflets with the upper surface being shown on the top right and the under surface being shown on the lower left.

The chart used in the identification of the colors is that of The Royal Horticultural Society (R.H.S. Colour Chart). The terminology which precedes references to the chart has been added to indicate the corresponding colors in common terms. The description is based on one year old specimens of the new variety which were observed during February while growing on their own roots in greenhouse at Le Cannet des Maures, Var, France.

Class: Miniature.

Plant:

Height.—Approximately 15 to 18 cm. on average above the pot when grown in 10 cm. pots.

*Habit.*—Bushy.

Branches:

*Color.*—Young stems: lettuce green, Green Group 143C. Adult wood: medium green, Yellow-Green Group 146B.

*Thorns.*—Size: small. Quantity: moderate. Color: pinkish on young stems and greenish changing to tan on adult wood.

Leaves:

*Petioles.*—Upper surface: striped, light green and more or less tinted with reddish coloration on young foliage and medium green on adult foliage with more or less glandular edges. Under surface: light green with a few tiny prickles.

*Stipules.*—Adnate, pectinate, wide and indented.

*Leaflets.*—Number: 3, 5(most often), and 7. Shape: spear-shaped. Serration: single and regular. Texture: consistent. General appearance: very dense and semi-dull. Color (young foliage): upper surface: light lettuce green, Yellow-Green Group 144B. Under surface: light lettuce green, Yellow-Green Group 144B, and slightly tinted with reddish coloration. Color (adult foliage): Upper surface: dark green, Green Group 139A. Under surface: medium green, Green Group 138B.

Inflorescence:

*Numbers of flowers.*—Approximately 1 to 3 per stem.

*Peduncle.*—Straight, rigid, covered with small pediculate glands, its length is approximately 2.5 cm. on average.

*Sepals.*—Upper surface: tomentose and greenish in coloration. Under surface: medium green, covered with small reddish pediculate glands, and the outer sepals may or may not be slightly appendiculated.

*Buds.*—Shape: conical. Length: approximately 1 cm. on average. Size: small. Color upon opening: Upper surface: dark currant red, Red Group 46A. Under surface: cardinal red, Red Group 53A.

*Flowers.*—Form: as a flat cup, and fully double. Diameter: approximately 2.5 to 3 cm. on average. Color (when opening begins): Upper surface: dark currant red, Red Group 46A. Under surface: light cardinal red, Red Group 53A. Color (when blooming): Upper surface: dark currant red, Red Group 46A. Under surface: cardinal red, Red Group 53A. Color (at end of blooming): Upper surface: dark currant red, Red Group 46A. Under surface: light cardinal red, Red Group 53A. Fragrance: none. Lasting quality: long. Petal number: approximately 40 to 43 on average. Petal form: the outer petals tend to be rounded and the inner petals tend to be oval and narrow and sometimes exhibit a central whitish vein. Petal texture: Consistent. Petal drop: good. Anthers: light ochre in coloration, located below the petals, some tend to be incomplete and may be bonded to petaloids. Stamen number: approximately 40 on average. Filaments: short, greenish in coloration, and of irregular heights. Pistil number: approximately 15 on average. Stigmas: straw-like in coloration. Styles: greenish in coloration, some lack a stigma and may exhibit a vegetative center. Receptacle: light green, smooth and in longitudinal section is funnel shaped.

Development:

*Vegetation.*—Very vigorous.

*Blooming.*—Abundant and continuous.

*Aptitude to bear fruit.*—Poor.

*Resistance to diseases.*—Good.

I claim:

1. A new and distinct variety of Miniature rose plant characterized by the following combination of characteristics:

(a) forms in abundance on a continuous basis attractive double long lasting blossoms which are currant red on the upper surface and cardinal red on the lower surface, (b) forms very vigorous vegetation, (c) exhibits a compact, regular, and bushy growth habit, (d) is well adapted to greenhouse forcing while growing in small containers and to the low light and low humidity growing conditions commonly encountered in the home, and (e) is not particularly affected by crytogamic diseases;

substantially as herein and described.

* * * * *

MEINOFRAI